United States Patent
Utku

(10) Patent No.: US 11,892,454 B2
(45) Date of Patent: Feb. 6, 2024

(54) METHOD FOR THE DIAGNOSIS OF ETOPOSIDE PRODRUG TREATABLE CANCER

(71) Applicant: CellAct Pharma GMBH, Dortmund (DE)

(72) Inventor: Nalan Utku, Munich (DE)

(73) Assignee: CELLACT PHARMA GMBH, Dortmund (DE)

( * ) Notice: Subject to any disclaimer, the term of this patent is extended or adjusted under 35 U.S.C. 154(b) by 0 days.

(21) Appl. No.: 16/110,007

(22) Filed: Aug. 23, 2018

(65) Prior Publication Data

US 2019/0086418 A1 Mar. 21, 2019

Related U.S. Application Data

(63) Continuation of application No. PCT/EP2017/054297, filed on Feb. 24, 2017.

(30) Foreign Application Priority Data

Feb. 24, 2016 (EP) .................................. 16157179

(51) Int. Cl.
| | | |
|---|---|---|
| G01N 31/00 | (2006.01) | |
| G01N 33/53 | (2006.01) | |
| G01N 33/574 | (2006.01) | |
| A61K 31/7048 | (2006.01) | |
| C12Q 1/6886 | (2018.01) | |

(52) U.S. Cl.
CPC ... *G01N 33/57438* (2013.01); *A61K 31/7048* (2013.01); *C12Q 1/6886* (2013.01); *G01N 33/57407* (2013.01); *G01N 33/57419* (2013.01); *C12Q 2600/106* (2013.01); *C12Q 2600/158* (2013.01); *G01N 2333/918* (2013.01); *G01N 2800/52* (2013.01)

(58) Field of Classification Search
None
See application file for complete search history.

(56) References Cited

U.S. PATENT DOCUMENTS 9,889,147 B2 * 2/2018 Utku ................. A61P 35/00
2003/0108484 A1 6/2003 Leyland-Jones

FOREIGN PATENT DOCUMENTS

| EP | 2558477 A1 | 2/2013 | |
|---|---|---|---|
| WO | WO-03048166 A1 * | 6/2003 | ........... C07D 493/04 |
| WO | 2011/127948 A1 | 10/2011 | |
| WO | 2012/167255 A1 | 12/2012 | |
| WO | WO-2012167255 A1 * | 12/2012 | ............ A61K 31/56 |
| WO | 2014/140072 A1 | 9/2014 | |

OTHER PUBLICATIONS

Xu et al. (Clinical Cancer Research, vol. 8, 2002, pp. 2605-2611).*
Capello etal. (JNCI, Journal of National Cancer Institute, 2015, vol. 107, No. 8, pp. 1-9). | (Year: 2015).*
Capello etal. (NCI, Journal of National Cancer Institute, 2015, vol. 107, No. 8, pp. 1-9). (Year: 2015).*
Xu et al. (Clinical Cancer Research, vol. 8, 2002, pp. 2605-2611) (Year: 2002).*
Capello et al. (INCI, Journal of National Cancer Institute, 2015, vol. 107, No. 8, pp. 1-9) (Year: 2015).*
Pape et al., Cancers, 2020, vol. 12, 3149, pp. 1-16. (Year: 2020).*
Goeppert et al. Scientific Reports, 2019, vol. 9, 4338, pp. 1-11. (Year: 2019).*
International Search Report and Written Opinion for Application No. PCT/EP2017/054297, dated Apr. 24, 2017. 8 pages.

* cited by examiner

*Primary Examiner* — Lisa V Cook
(74) *Attorney, Agent, or Firm* — SALIWANCHIK, LLOYD & EISENSCHENK

(57) ABSTRACT

The present invention pertains to a diagnostic and therapeutic method for assessing whether a patient is susceptible to the treatment of an ester-prodrug. The methods of the invention include the analysis of carboxyesterase 2 (CES2)-expression in tumor samples as a predictive value for the assessment of treatment success with an ester-prodrug of a chemotherapeutic agent. Alternatively, the invention provides methods involving the analysis of the urinary ratio of the prodrug and the active therapeutic as another predictive value for assessing treatment susceptibility.

5 Claims, 4 Drawing Sheets

A

Score       7             8

B

Score    0      5      6      7      8

A

B

METHOD FOR THE DIAGNOSIS OF ETOPOSIDE PRODRUG TREATABLE CANCER

CROSS-REFERENCE TO RELATED APPLICATIONS

Figure 1:
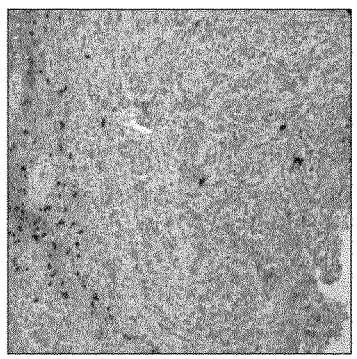
Figure 1:
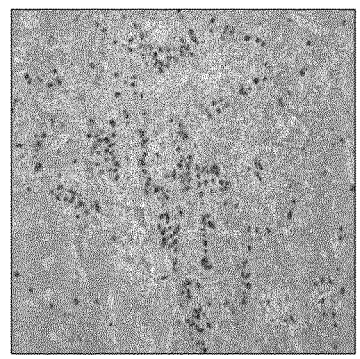
Figure 1:
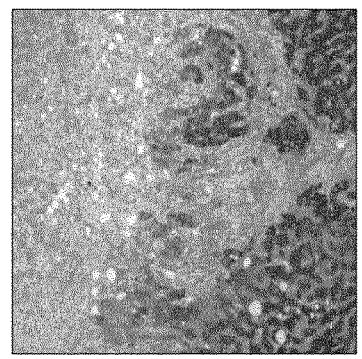
Figure 1:
Figure 1:
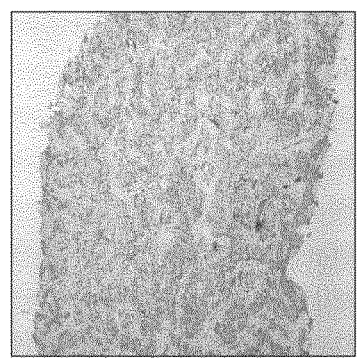
Figure 1:
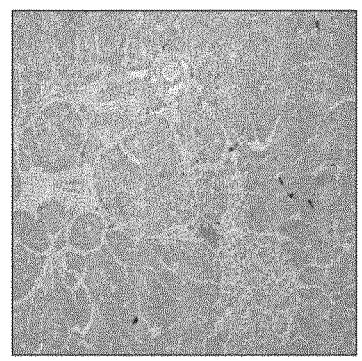

This application is a continuation application of International Application No. PCT/EP2017/054297, filed on Feb. 24, 2017, which claims priority of European Patent Application No. 16157179.9, filed on Feb. 24, 2016. The entire contents of each of the aforementioned applications are incorporated herein by reference.

FIELD OF THE INVENTION

The present invention pertains to a diagnostic and therapeutic method for assessing whether a patient is susceptible to the treatment of an ester-prodrug. The methods of the invention include the analysis of carboxyelesterase 2 (CES2)-expression in tumor samples as a predictive value for the assessment of treatment success with an ester-prodrug of a chemotherapeutic agent. Alternatively, the invention provides methods involving the analysis of the urinary ratio of the prodrug and the active therapeutic as another predictive value for assessing treatment susceptibility.

DESCRIPTION

For many cancer treatments, treatment success varies between individual patients. These variations may be due to natural or acquired resistances of a cancer disease against certain chemotherapeutic agents. Multi-Drug Resistance Tumor cells become resistant against chemotherapy after prolonged treatment. The resistance may be intrinsic or acquired resistance and is known to be a major contributing factor to failure in cancer treatment. Clinical drug resistance often presents as a multi-drug resistance (MDR) phenotype, characterized as de novo resistance to a variety of structurally diverse drugs or as developed cross-resistance to chemotherapeutic agents that have never been used in previous chemotherapy.

Although the cellular basis underlying drug resistance is not fully understood, several factors have been identified that contribute to its development. These include drug efflux mechanisms, increased drug inactivation (e.g. glutathione-S-transferase and resistance to allkylating agents), drug target mutation (topoisomerase mutation), altered DNA repair and resistance to apoptosis (p53 mutation, bcl-2 over expression etc.).

Many drugs are metabolized by cytochrome P450 (CYP) isozymes. Some drugs are rapidly degraded by esterase enzymes in the gastrointestinal (GI) tract, liver and/or central circulation before arriving at their target sites or reaching certain levels in the central circulation to confer therapeutic effect. Two pharmacokinetic parameters, i.e., the area under the plasma concentration versus time curve (AUC) and peak plasma concentration (Cmax) are commonly used to assess the absorption pharmacokinetics of a drug. The degree of improvement of absorption kinetics and the availability of a drug in the central circulation (i.e., bioavailability), however, are assessed mainly by using AUC of the drug. The absorption kinetics and oral bioavailability of some drugs, which are therapeutically active but are poorly absorbed, can be improved by the synthesis of their ester prodrugs which are more readily absorbed from the GI tract. Ester prodrugs are prodrugs having ester moieties. Once absorbed, ester prodrugs undergo hydrolysis to generate active drugs under the action of the esterase. Prodrugs are used in cancer treatment to enhance bio availability of the active compound. However, not all patients convert the administered prodrug into its active form with the same conversion efficiency.

Biliary tract cancer (BTC) is a neoplasm that accounts for 3% of all gastrointestinal cancers and 15% of all primary liver cancers. During the last two decades, the incidence of BTC is rising, mainly due to an increase in the intrahepatic form (Khan, S. A. et al., "Cholangiocarcinoma," Lancet, 366:1303-14 (2005); Patel, T. et al., "Cholangiocarcinoma," Nat Clin Pract Gastroentel Hepatol, 3:33-42 (2006)). North Thailand has the highest incidence (Shaib, Y. et al., "The epidemiology of holangiocarcinoma," Semin Liver Dis, 24:115-125 (2004)). Only chance to cure is complete surgical resection. For complete resection, diagnosis in early stage is important, but difficult. Even with margin free resection, 5-year survival figures only reach 20% to 40% (Jarmagin, W. R., et al., "Surgical management of cholangiocarcinoma," Semin Liver Dis, 24:18 (2004); Gores, G. J., "Cholangiocarcinoma: current concepts and insight," Hepatology, 37:961-969 (2003)). Unresectable disease usually shows 6-month to 1-year survival time (Jarmagin, W. R., et al., "Surgical management of cholangiocarcinoma," Semin Liver Dis, 24:18 (2004)). Almost for one-third of the patients of BTC it is too late for resection. Therefore, there is a need to establish a diagnostic process at the early stage of BTC.

Currently, diagnosis of BTC depends on images of the biliary tree such as computed tomography or ultrasonography or endscopic retrogradal cholangiograpy (ERC) in patients having clinical symptoms. Brush cytology by ERC can make a tissue diagnosis, but sensitivity is poor because of rich desmoplastic nature of BTC (Gores, G. J., "Cholangocarcinoma: current concepts and insight," Hepatology, 37:961-969 (2003); Abu-Hamda, E. M., et al., "Endoscopic management of cholagiocarcinoma," Semin Liver Dis, 4:165-175 (2004)). Consequently clinicians often elucidate other diagnostic clues of malignancy, and tumor markers provide more information.

Therefore, there is a need in the art for methods for the prediction of treatment success of a therapy involving the use of prodrugs. The invention also seeks to provide better diagnostics for assessing treatment success for biliary tract cancer patients.

The molecular target of CAP7.1 is, as of etoposide, the DNA enzyme topoisomerase II. The assumed reason for CAP7.1's more favourable therapeutic and side effect profile is that the cleavage enzyme, Carboxyl esterase 2 (CES2), being instrumental for the prodrug conversion (Utku et al., unpublished), is primarily expressed in certain tissues such as biliary tract tumours. The prodrug CAP7.1 is preferentially converted by CES2 to its parent moiety in the periphery, during liver passage and in the colon after enterohepatic recirculation. Immunohistology staining of various gastrointestinal tumours, including BTC, was performed in order to address the question how the spatial expression of CES2 within the tumour and non-tumour intestinal tissues might affect the therapeutic efficacy of CAP7.1.

The analysis of the expression of CES2 in gastrointestinal tumours revealed liver tissue and peripheral blood mononuclear cells as important check points of prodrug conversion. As biliary cancers are derived within the liver (intrahepatic BTC) or closed area of the liver (extra-hepatic BTC), the CES2 expression in the liver is beneficial for the use of CAP7.1 in BTC as it might contribute to drug accumulation in close proximity to the tumour environment.

However, the CES2 expression within the tumour is heterogeneous and in some cases lower than in the tumour-adjacent tissue. It was shown that, in addition to the tumour cells themselves, immune cell infiltrates in the immediate vicinity of some tumours express high levels of CES2. Therefore, in certain patients, non-tumourous tissue adjacent to the tumour can be a relevant source of CES2. Not all patients demonstrated intra-tumour infiltrates in biopsies. Although a CES-mediated first pass effect within the liver might significantly contribute to the systemic availability of an esterase activity-dependent bioactive drug, the main tumour-specific effect might be increased when also mediated by its intra-tumour release. This would lead to accumulation of the respective drug in tumour tissue independently and/or in addition to the expression of CES2 in tumor infiltrating lymphocytes or liver.

Translated into the clinic, CES2+ BTC cases might benefit several fold from the therapy with CAP7.1: 1) increase of local drug levels, 2) CES+lymphocytes and 3) CES2+ liver tissue surrounding biliary tumours.

Thus, the above problem is first solved by a method of diagnosing and/or stratifying a patient suffering from cancer, the method comprising the steps of
  a. Providing a tumor sample of the patient,
  b. Determining the expression of carboxylesterase 2 (CES2) in the tumor sample, wherein a lack of expression of CES2 in the tumor sample indicates the risk of a patient to not benefit from a treatment with an ester-prodrug of a chemotherapeutic agent, and wherein the expression of CES2 in the tumor sample indicates that the patient will benefit from a treatment with an ester-prodrug of a chemotherapeutic agent.

In an alternative aspect, the invention provides a method of assessing if a cancer patient is a responder to treatment with an ester prodrug of a chemotherapeutic agent, the method comprising the step of
  a. Providing a tumor sample of the patient,
  b. Determining the level of CES2 expression in the tumor sample, wherein the expression of CES2 in the tumor sample indicates that the patient is a responder to treatment with the ester prodrug of a chemotherapeutic agent.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; biliary tract cancer, breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, thymus carcinoma, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; neuroblastoma, bone cancer; soft tissue sarcoma; and thyroid carcinoma.

Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

However, preferred embodiments of the invention pertain to gastro intestinal cancers that are CES2 positive. Most preferred is biliary tract cancer (BTC).

A tumor sample in context of the invention is preferably a sample of tumor cells. However, in context of the invention the term "tumor sample" shall in addition include also samples of tumor adjacent tissue. The reason is that the present invention shows that tumor adjacent tissue in some patients shows elevated levels of CES2 expression. The nature of the sample will vary according to the type of cancer and may range from a blood or serum sample to tissue samples. Preferred are tissue samples acquired by biopsy, in particular for embodiments pertaining to biliary tract cancer.

The level of expression of CES2 in the tumor sample is preferably determined immunological, preferably by antibody staining. However, the invention may also make use of other methods for the detection of CES2 expression such as, but not limited to, mass spectroscopic methods, or PCR based technologies. The level of expression of CES2 may be compared with a control or reference in order to assess whether the tumor expresses CES2 or not, or whether the tumor has a reduced or increased CES2 expression. For example, the control or reference value is a predetermined value of CES2 expression in a CES2 negative reference tumor sample.

The term "prodrug" as used herein means a chemical derivative of a drug molecule (a pharmaceutically active ingredient) that undergoes a metabolic transformation within the body of a subject thus releasing the active moiety. The term "ester prodrug" is construed accordingly as an inactive ester form (i.e. —CO—OR; where R is an organic substituent), of a pharmaceutically active ingredient which undergoes transformation, such as hydrolysis, within the body of a subject to release the active drug. An ester prodrug is preferably transformed by CES2.

The prodrug is in preferred embodiments an etoposide prodrug, for example a compound with the formula: I,

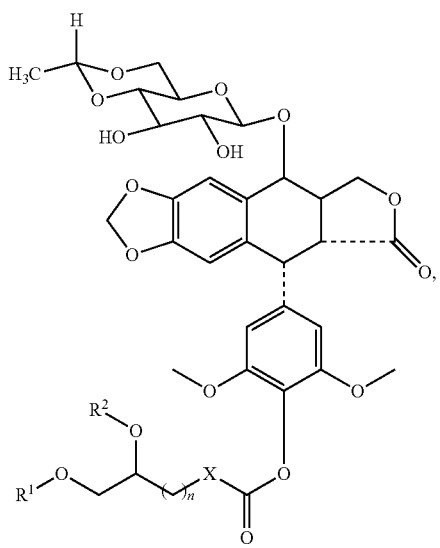

(I)

wherein X is selected from the group consisting of O, NH and S, n is 0, 1 or 2, and $R^1$ and $R^2$ are independently selected from the group consisting of H, methyl and ethyl, or together form a group $CR^3R^4$ wherein $R^3$ and $R^4$ are independently selected from the group consisting of H, methyl and ethyl, or a pro-drug, derivative solvate or salt thereof.

Preferably, the prodrug of the invention is selected from

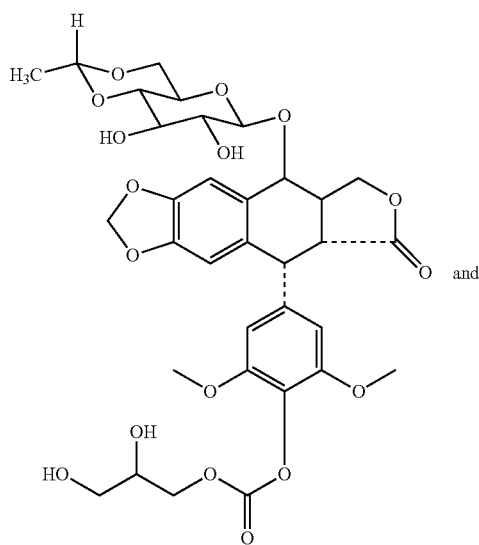

and

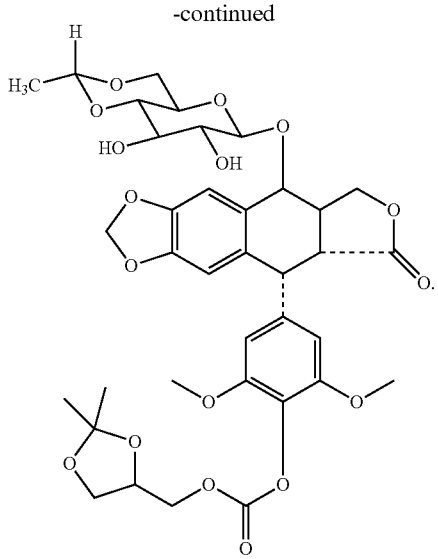

Preferably the compound of the present invention is CAP7.1.

In one preferred aspect the invention also provides the above mentioned prodrugs for use in the herein disclosed methods.

Another aspect of the invention further pertains to a method of monitoring a treatment with an ester-prodrug of chemotherapeutic in a cancer patient, comprising a step of determining the ratio of the ester-prodrug of chemotherapeutic and the chemotherapeutic (Prodrug:active compound=urinary ration UR) in a urine sample obtained from the patient during the treatment, wherein a reduced UR compared to a control or reference value indicates a response to the treatment and that the treatment with the ester-prodrug should be continued.

The reference or control value in this context refers to a UR in a patient not responding to a treatment with the ester-prodrug of chemotherapeutic.

In one alternative aspect the invention further pertains to a method of monitoring a treatment with an ester-prodrug of chemotherapeutic in a cancer patient, comprising a step of determining the ratio of the ester-prodrug of chemotherapeutic and the chemotherapeutic (Prodrug:active compound=urinary ration UR) in a urine sample obtained from the patient during the treatment, wherein an increased UR compared to a control or reference value indicates that the patient is a non-responder to the treatment and that the treatment with the ester-prodrug should be discontinued.

In this aspect the reference or control value in this context refers to a UR in a patient responding to a treatment with the ester-prodrug of chemotherapeutic.

In order to determine the UR, the treatment comprises a step of administration of the ester-prodrug to the patient.

In some embodiments, a low UR in the sample of the patient (of less than 10, more preferably less than 5, more preferably less than 4, 3, 2, 1, 0.9, 0.8, 0.7 0.6 0.5, 0.4, 0.3, 0.2, 0.1, preferably less than 0.09, 0.08, 0.07, 0.06, most preferably less than 0.05), indicates a response to the treatment and that the treatment with the ester-prodrug should be continued.

In some embodiments, a UR in the sample of the patient of less than 0.5 indicates a response to the treatment and that the treatment with the ester-prodrug should be continued.

In some embodiments, a UR in the sample of the patient of less than 0.1, preferably less than 0.05, indicates a response to the treatment and that the treatment with the ester-prodrug should be continued.

The methods of the herein described invention are in preferred embodiments in-vitro or ex-vivo methods.

A urine sample obtained from the patient in accordance with the invention is preferably a urine sample that was collected over a certain time period. For example in some embodiments the time period is at least 12 hours, preferably at least 24 hours.

In addition to the determination of the UR, the invention also provides methods that comprise both the determination of the UR and a step of determining expression of CES2 in a tumor sample from the patient. The predictive value of a combination of CES2 expression and UR is even higher than the single predictive values for both markers.

Another aspect of the invention then pertains to a method of treating a cancer of a patient, said method comprising
  a. assessing if the cancer patient is a responder to a treatment with an ester-prodrug of a chemotherapeutic agent by the method of any of claims 2 to 6, and
  b. (i) treating the cancer patient with the ester-prodrug of a chemotherapeutic agent if the patient has a reduced risk for not being a responder to treatment with the ester-prodrug of a chemotherapeutic agent or
  (ii) treating the cancer patient with a treatment regimen which comprises a treatment which is different from an ester-prodrug of a chemotherapeutic agent if the patient has an increased risk for not being a responder to treatment with the ester-prodrug of a chemotherapeutic agent.

The the ester-prodrug of a chemotherapeutic agent is preferably an ester prodrug of etoposide, preferably CAP7.1. The cancer is as defined above, or preferably biliary tract cancer (BTC).

Yet a further aspect pertains to a method of treating a cancer of a patient, said method comprising
  a. Administering to the patient a therapeutically effective amount of an ester-prodrug of a chemotherapeutic agent,
  b. Obtaining an urine sample from the patient,
  c. Determining the urinary ratio of the ester-prodrug of a chemotherapeutic agent and the chemotherapeutic agent in the urine sample.

A decreased urinary ratio compared to a control or reference value indicates that the cancer of the patient is susceptible to the treatment with the ester-prodrug of a chemotherapeutic agent. Preferably, a decreased urinary ratio compared to a control or reference value indicates to continue with the treatment which comprises the administration of the ester-prodrug of a chemotherapeutic agent, or adjustment of the dose to avoid side effects or wherein an increased urinary ratio compared to a control or reference value indicates to discontinue a treatment comprising the administration of the ester-prodrug of a chemotherapeutic agent.

In the context of the herein described invention the term "patient" shall refer to animals or humans. Preferably an animal patient is a mammal, more preferably a farm animal, such as bovine animals, horses, chicken, pigs, cheep, goats etc., or a pet animal such as dogs, cats, birds, rodents etc. Most preferably the patient is a human patient.

Administration of the compounds, products and/or pharmaceutical compositions to a patient suffering from a disease or disorder is considered successful (treatment success) if any of a variety of laboratory, radiology or clinical results is achieved. For example, administration is considered successful one or more of the symptoms associated with the disease or disorder is alleviated, reduced, inhibited or does not progress to a further, i.e., worse, state. Administration is considered successful if the disorder enters remission or does not progress to a further, i.e., worse, state. Preferably, in context of the herein described invention a successful treatment is achieved when the amount, number, or rate of proliferation of the cancer cell sub- population in a patient is reduced or dampened. Such a result provides for a better chance of the treated patient to avoid cancer relapse after treatment or the formation of further metastasis.

A cancer according to the herein described invention may also be a colorectal cancer.

Yet in another aspect of the invention there is provided a method of treating a solid tumor disease in a subject, the method comprising the steps of:
  a. Providing a sample of tumor tissue of the patient, and/or a sample of healthy tissue (directly) adjacent to the tumor in the patient,
  b. Determining the level of expression of CES2 in a tumor tissue cell or a tumor tissue infiltrating leukocyte, of said sample of tumor tissue of the patient, and/or
  c. Determining the level of expression of CES2 in a healthy tissue cell and/or in a healthy tissue infiltrating leukocyte, of said sample of healthy tissue adjacent to the tumor in the patient; and
  d. if CES2 compared to a control is, or is significantly more, expressed in a tumor tissue cell or a tumor tissue infiltrating leukocyte of said sample of tumor tissue of the patient, and/or CES2 compared to a control is, or is significantly more, expressed in a healthy tissue cell and/or in a healthy tissue infiltrating leukocyte, of said sample of healthy tissue adjacent to the tumor in the patient, administering a therapeutically effective amount of an ester pro-drug of a chemotherapeutic agent to the patient; or if CES2 compared to a control is not, or significantly less, expressed in a tumor tissue cell or a tumor tissue infiltrating leukocyte of said sample of tumor tissue of the patient, and/or CES2 compared to a control is not, or significantly less, expressed in a healthy tissue cell and/or in a healthy tissue infiltrating leukocyte, of said sample of healthy tissue adjacent to the tumor in the patient, administering a therapeutically effective amount of a chemotherapeutic agent which is not an ester prodrug to the patient.

Also provided is a method for determining a treatment for a patient having a solid tumor disease, the method comprising the steps of
  a. Providing a sample of tumor tissue of the patient, and/or a sample of healthy tissue (directly) adjacent to the tumor in the patient,
  b. Determining the level of expression of CES2 in a tumor tissue cell or a tumor tissue infiltrating leukocyte, of said sample of tumor tissue of the patient, and/or
  c. Determining the level of expression of CES2 in a healthy tissue cell and/or in a healthy tissue infiltrating leukocyte, of said sample of healthy tissue adjacent to the tumor in the patient; and
  d. if CES2 compared to a control is, or is significantly more, expressed in a tumor tissue cell or a tumor tissue infiltrating leukocyte of said sample of tumor tissue of the patient, and/or CES2 compared to a control is, or is significantly more, expressed in a healthy tissue cell and/or in a healthy tissue infiltrating leukocyte, of said sample of healthy tissue adjacent to the tumor in the patient, a therapeutically effective amount of an ester prodrug of a chemo-therapeutic agent is determined as a treatment for the patient; or if CES2 compared to a control is not, or significantly less, expressed in a tumor tissue cell or a tumor tissue infiltrating leukocyte of said sample of tumor tissue of the patient, and/or CES2 compared to a control is not, or significantly less, expressed in a healthy tissue cell and/or in a healthy tissue infiltrating leukocyte, of said sample of healthy tissue adjacent to the tumor in the patient, a therapeutically effective amount of a chemotherapeutic agent which is not an ester prodrug, is determined as a treatment for the patient.

A solid tumor disease is colorectal cancer (CRC) preferably.

In a preferred embodiment, the ester prodrug of a chemotherapeutic agent is Cap7.1, or a derivative, or salt or solvate thereof, as described herein elsewhere.

Providing a tissue sample of the patient in some embodiments preferably involves the resection of tumor tissue and/or together with adjacent healthy tissue.

In context of the herein described invention, a sample of tissue adjacent to the tumor comprises preferably at least one non-tumor cell which directly surrounds (contacts) the tumor tissue, preferably comprising cells of the lamina propria.

In some embodiments, the expression of CES2 is determined immunohistochemically, preferably by using a CES2 specific antibody, such as #ab64867 polyclonal rabbit, Abcam, Cambridge, UK. The grading of CES2 expression may in preferred embodiments be performed as described in the example section of this disclosure.

In other preferred embodiments of the above two methods of the invention, the CES expression is determined in leukocytes infiltrating into tumor tissue and/or adjacent healthy tissue to perform the inventive treatment or therapy determination as disclosed herein.

The term "leukocytes" as used herein refers to granulocytes including neutrophils, eosinophils, basophils, monocytes, and lymphocytes including B cells and T cells and unless otherwise specified, platelets. The term "leukocytes" in context of the invention in some preferred embodiments pertains to plasma cells.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: CES2 Tissue Staining: A: CAP7 responder patients; B: CAP7 non-responder patients FIG. 2: Urinary Ratios of subjects Treated with CAP7.1 Groups: 1=Patients with disease control & partial response with UR<0.0416 and CES+; 2=patients with SD with UR>0.0416 and CES + or not determined 3 =Patients with PD with UR>0.0416 and CES−/+ or not determined FIG. 3: Scoring of CES expression. (A) Sections of normal tissue or (B) TMA spots from graded CRC were stained for CES 2 by immunohistochemistry (brown); nuclei with hematoxylin (blue). (A) Characteristic CES-2 distribution in normal colon tissue with strong expression in epithelial cells along the crypts. (B) Score 0: all tumor cells devoid of CES-2 expression; score 5: strong CES-2 expression in about 20% of the tumor cells; score 6 medium CES-2 expression in up to 90% of tumor cells; score 7: strong CES-2 expression in up to 90% of tumor cells; score 8: strong CES-2 expression in over 90% of tumor cells. Representative images; original magnification×100. Bars represent 100 μm.

Figure 4:
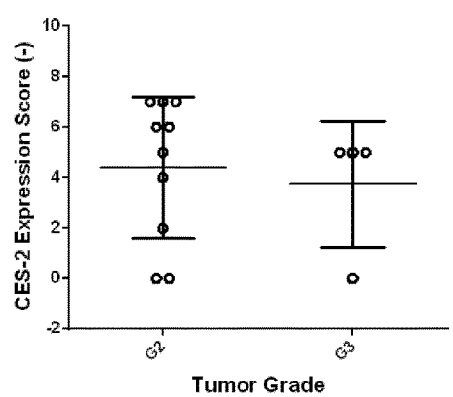
Figure 4:
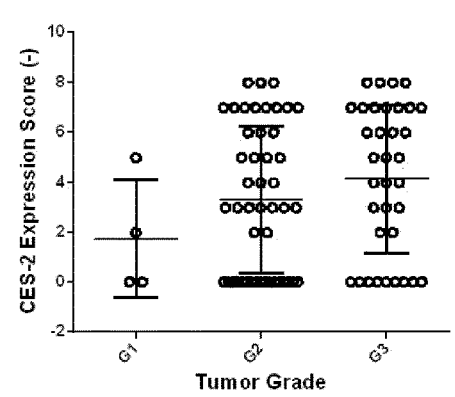

FIG. 4: CES-2 expression in CRC. Samples of tumor and normal colon tissue from patients with CRC of different grades were stained for CES-2 by immunohistochemistry. The CES-2 expression of the tumor and or the epithelial cells was scored. (A) CES-2 expression scores from resected CRC tissue of tumor grades G2 (n=10) and G3 (n=4). Scatterplot with mean+/−SD. (B) CES-2 expression scores from TMA spots of CRC tissue from tumor grades G1 (n=4), G2 (n=47) and G3 (n=35). Scatterplot with mean+/−SD.

Figure 5:
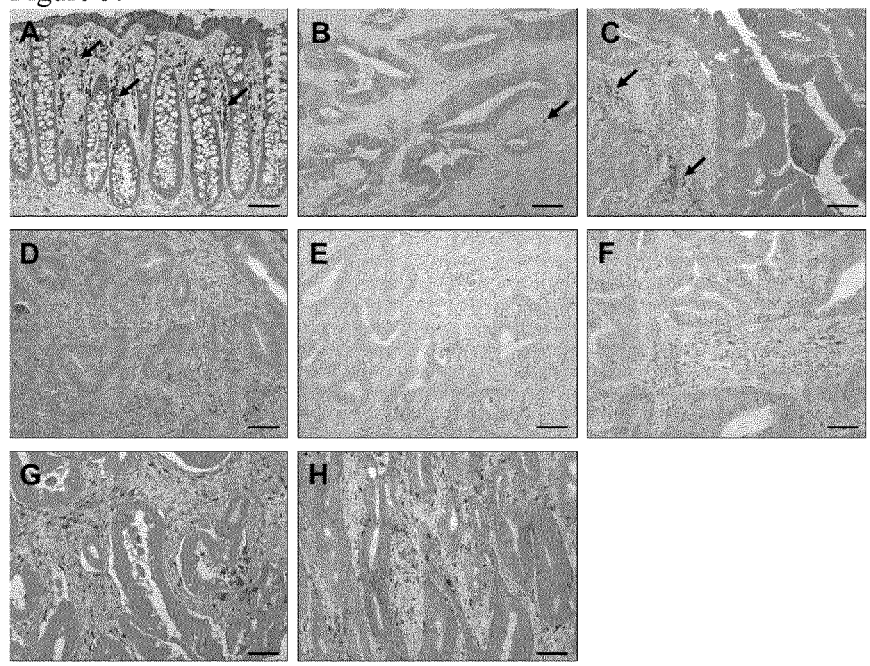

FIG. 5: Cell type and localization of CES 2+ cells within and around the tumor tissue in CRC. Immunohistochemistry for CES-2 expression or proteins for different immune cell types was carried out with samples of resected CRC tumor tissue from a patient with grade 2 CRC. Nuclei were stained with hematoxylin. (A) Normal tissue areas or (B, C) tumor regions were stained for CES-2 and arrows indicate the abundance of CES-2+ cells. Tumor tissue was stained for (D) CD11b+ immune cells (red), (E) MPO+ neutrophils (red), (F) CD20+ B cells (red) and CD3+ T cells (brown), (G) CD163+ macrophages (red) and CES-2+ cells (blue) or (H) CD138+ plasma cells (red) and CD68+ macrophages (brown). Representative images for n=10 patients with grade 2-3 CRC; original magnification ×100. Bars represent 100 μm.

Figure 6:
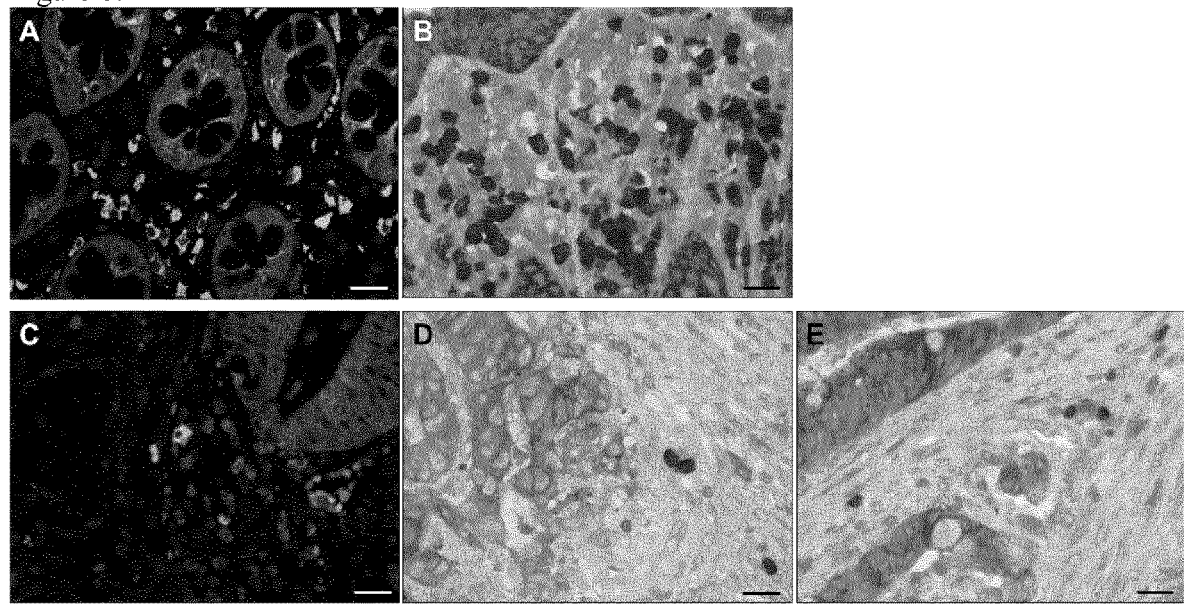

FIG. 6: CES-2+ plasma cells in intestinal tissues from CRC. (A, B) Normal colon tissue from CRC patients or (C E) CRC tumor tissue were stained (A, C) for CES-2 (red) and CD138 (green) by immunofluorescence or (B, D, E) CES-2 (brown) and MUM-1 (red) by immunohistochemistry. Nuclei were stained with DAPI (A, C) or hematoxylin (B, D, E) and appear blue. Representative images for n=10 patients with grade G2-3 CRC; original magnification ×400. Bars represent 20 μm.

Responder=patients show therapeutic benefit and received at least two cycles of CAP7.1

EXAMPLES

Since the prodrug CAP7.1 requires conversion to active etoposide, local and systemic CES2 expression may be a determining factor for the efficacy and safety of CAP7.1.

The IHC assessment of CES2 protein expression could possibly lead to prediction of response and tolerability of CAP7.1 and could be utilized for patient stratification in post-marketing studies. Assessment of the Urinary Ratios (UR) of CAP7.1: etoposide might provide information about the metabolism of CAP7.1 in patients with BTC, which might potentially support therapeutic monitoring of the drug to optimize drug levels.

The major determinants in the conversion of CAP7.1 into etoposide are the human carboxyl esterases, especially CES2. Thus, conversion of CAP7.1 to etoposide via CES2 at the tumour site may provide benefit, especially to those patients who have CES2 highly expressed in their tumour. Moreover, the systemic conversion rate may also be of importance.

It is therefore proposed to measure CES2 expression in a tumour biopsy to assess expression in tumour and in peripheral mononuclear cells (PBMC) to assess systemic expression. Moreover, the urinary ratio of CAP7.1 and etoposide will provide an indication for systemic conversion of CAP7.1 to etoposide.

Example 1

CES2 Tumor Expression Correlates with CAP7.1 Treatment Success

In a new study protocol, the staining of CES2 of tumour tissue samples was introduced to test the hypothesis. Therefore data from 7 patients treated with CAP7.1 and one patient as BSC control is available on CES2+ expression in BTC tumours (Table 1).

TABLE 1

Expression of CES2 in patients with BTC

| Patient | CES2 staining | Response | Etoposide $AUC_{(0-\infty)}$ µg/ml hr | CAP7.1/Etoposide Urinary Ratio |
|---|---|---|---|---|
| DE-1 | 2++ | PR | NC | 0.86 |
| DE-2 | 1+ | SD | 20.35 | 0.01 |
| DE-3 | 3+ | SD | 10.22 | 0.01 |
| DE-4 | 3+ | SD | NC | 0.01 |
| DE-5 | 3+ | PD | 14.12 | n.a. |
| DE-6 | — | PD | NC | n.a. |
| DE-7 | — | PD | NC | 0.11 |

NC/n.a.: Not calculated or not available

CES2 stainings of tumor samples is shown in FIG. 1. FIG. 1A shows that a high CES2 expression was observed in patients responding to CAP7.1. treatment, whereas a low CES2 expression was observed in non-responder patients (FIG. 1B).

Example 2

Figure 2:
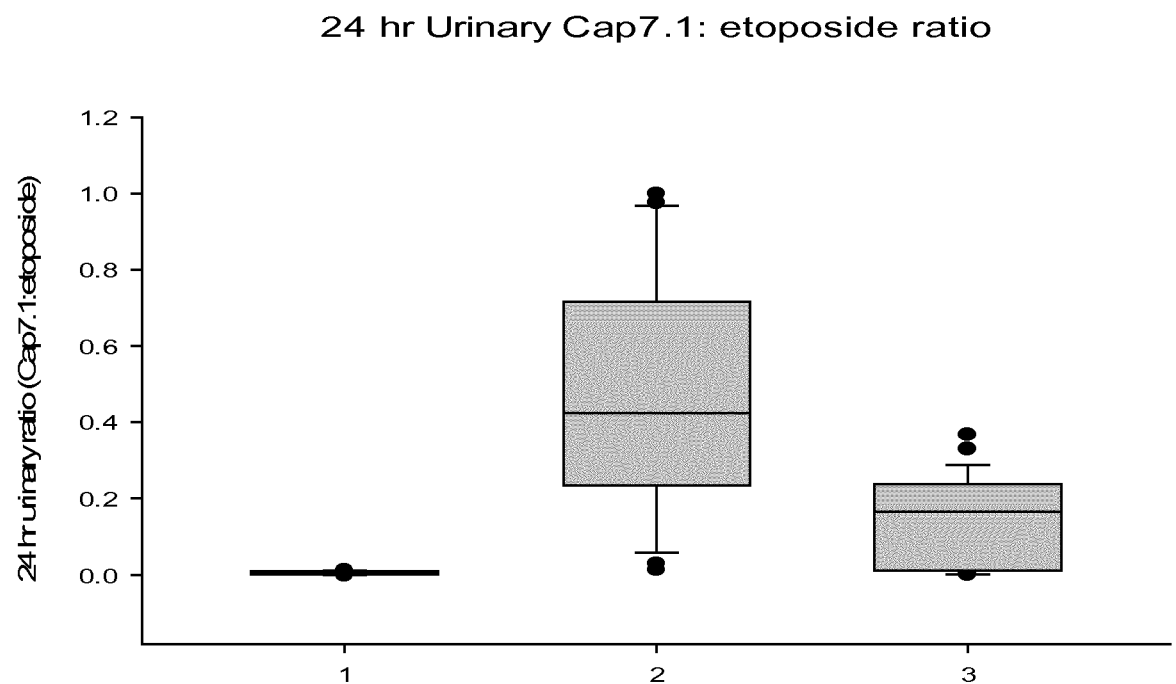

Urinary Drug Analysis of CAP7.1 and Etoposide in the Phase I and Phase II Studies An evaluation of the Phase I and II data with respect to the conversion of CAP7.1 to etoposide and the urinary ratio of CAP7.1: etoposide (UR) in 24 h urine collection was undertaken. The urine collection data for the patients with disease control including SD (Stable disease) and PR (partial response) response to CAP7.1 and non-responders (patients with progressive disease (PD)) to CAP7.1 with respect to UR and CES2 expression were evaluated. Results are depicted in FIG. 2: UR shows that the subjects responding to CAP7.1 with high CES2 expression fall into two groups, one with a low UR and one with a higher UR.

The group with the low UR had a median (range) of 0.00716 (0.0121). The 75% quartile for this group was 0.0416. Thus any responder with high CES2 expression with a UR below 0.0416 was classified as a low UR subject and any responder with a high expression of CES2 but a UR higher than 0.0146 as a high UR subject.

TABLE 2

Subjects responding to CAP7.1 with CES2 expression

| Groups | n | Total CAP7.1 (mg) | Total Eto (mg) | UR | Total Drug Recovered (mg) |
|---|---|---|---|---|---|
| 1 | 10 | 0.56 (0.01-1.42) | 75.88 (50.61-165.80) | 0.01 (0.01-0.01) | 76.15 (51.10-225.50) |
| 2 | 22 | 19.95 (0.15-91.93) | 56.35 (16.80-153.40) | 0.42 (0.01-1.70) | 76.53 (30.02-173.31) |
| 3 | 26 | 14.45 (0.01-25.72) | 89.26 (2.26-136.30) | 0.17 (0.01-0.47) | 101.91 (3.31-160.5) |

All values reported are the median and ranges;
n = number of urine samples
Group 1 SD with CES2+ tumours and UR < 0.0416
Group 2 SD/PR with CES2 + tumours/no CES2 data and UR > 0.0416
Group 3 PD with CES2 − tumours/no CES2 data and UR > 0.0416

As can be seen from table 2, subjects having a low urinary ratio a very likely to be CAP7.1 responders.

Example 3

Expression of CES-2 in Tumor Cells Does Not Correlate with the Tumor Grade in Colorectal Carcinoma Recent immunohistochemically analyses indicate a broad range of CES-2 expression levels in CRC [5, 6]. To get more information about the base level expression of CES, non-inflamed colon tissue from the resection area of surgery was analyzed using immunohistochemistry. The findings showed that the expression of CES-2 in epithelial cells increased along the crypt in normal human colon with highest expression in the surface epithelium, whereas expression was completely diminished at the base of the crypt and (FIG. 3B). This suggests that CES-2 expression increases during differentiation of epithelial cells.

An initial study using a small number of patient samples (n=14) from grade G2 and G3 CRC tumor samples showed no significant correlation between CES-2 expression scores and tumor grades (Mann-Whitney test; FIG. 4A). Screening 86 samples (cecum: n=8, colon: n=56, rectum: n=22) from microarrays, representing 86 patients, resulted in CES-2 expression scores of 0-8 with no significant correlation to the tumor grade (Kruskal-Wallis test; FIG. 4B). Thus, the expression levels of CES-2 within the tumor cells did not associate to the state of the tumor.

As the TMA samples are only from a single location within the tumor, it was important to ensure that the samples scoring 0 were representative of the CES-2 expression pattern in the larger areas of the corresponding resected tumor tissues. Only half of the CRC cases revealed identical CES-2 expression scores from the TMA and from larger areas of the resected tumors tissues (not shown). As some tumors were completely devoid of the CES-2 protein, we tested for the expression of CES-1 as a potential compensatory mechanism. All tumor spots from the TMA (n=86) and all larger sections of resected tumor tissue also tested (n=14) were negative for CES-1. Additionally, NEC of the cecum, the colon and the rectum tested negative for both CES-1 and CES-2 (not shown).

In CRC, CES-2 expression was also heterogeneous within single tumors. Hence, we focused on patient-matched samples (n=41) to compare the expression of CES-2 between normal colon tissue areas retrieved during surgical resection of the tumor and the cells from CRC tumors of all grades. Epithelial cells showed moderate to strong CES-2 expression ranging between score 5 and 8. The overall expression of CES-2 was significantly higher in normal epithelial cells compared with epithelial cell-derived tumor cells in CRC (p=0.0323 with Wilcoxon matched-pairs signed ranked test).

Example 4

Immune Cells in the Immediate Vicinity of the Tumor Express CES-2

Examination of the lamina propria of samples taken from non-cancerous areas distant from CRC surgery showed a moderate infiltration with leukocytes, and a number of the leukocytes strongly expressed CES-2 (FIG. 5A). In some tumors, the tissue immediately surrounding the cancerous lesion exhibited only sporadic CES-2+ cells (FIG. 5B), while in other tumors the tissue was heavily infiltrated (FIG. 5C). The number of CES-2+ cells in the tissue surrounding the tumor was independent of the level of CES-2 expression in the tumor cells. Leukocytes directly infiltrating the tumor were always negative for CES-2, whereas CES-2 expression in the leukocytes located close to the tumor was consistently high (FIG. 5B, C). Immunohistochemical analysis of the tissues surrounding the tumors, looking at CD11b+ myeloid cells (FIG. 5D), MPO+neutrophils (FIG. 5E), CD3+ T cells and CD20+ B cells (FIG. 5F), CD163+ macrophages (FIG. 5G) as well as for CD68+ macrophages and CD138+ plasma cells (FIG. 5H) revealed the presence of various types of leukocytes.

Example 5

Plasma Cells in the Tumor Vicinity Contribute to Production of CES-2 in CRC

Specifically addressing the plasma cell compartment, tissues were co-stained for CES-2 and for CD138, which is expressed on plasma and epithelial cells [15], and MUM1 expressed in nucleus and cytoplasm of mostly plasma cells [16], respectively. Fluorescence (FIG. 6A, C) and bright-field microscopy (FIG. 6B, D, E) confirmed plasma cells as the producers of CES-2 in the lamina propria of normal colon tissues from patients with CRC (FIG. 4A, B) and in the vicinity of the CRC (FIG. 6C, D). Although all CES-2+ cells were plasma cells, not all plasma cells expressed CES-2; plasma cells devoid of CES-2 were also present in the tissue surrounding the tumor (FIG. 6E).

These observations suggested that plasma cells in the immediate surroundings of the tumor were an important source of the enzymatic activity of CES in situ.

Materials and Methods

Human tissue and blood samples. The following archived formalin-fixed paraffin-embedded (FFPE) samples were retrieved from the tissue bank of the Charité—Universitäts-medizin, Zentrale Biomaterialbank (ZeBanC; http://biobank.charite.de/service/) (Berlin, Germany): intestinal tissue from patients with CRC including tissue microarray (TMA; Table 2), with neuroendocrine carcinomas (NEC) of the large intestine (cecum, n=2; colon, n=3; rectum, n=2), Crohn's disease (CD, n=4) or ulcerative colitis (UC, n=5); liver tissue from patients with hepatocellular (HCC, n=5) or cholangiocellular carcinoma (CCC, n=6); normal colon tissue from patients with CRC. Normal tissues were taken from resection margins with normal intestinal morphology assessed after hematoxylin/eosin (H&E) staining. Whole blood samples from healthy donors were obtained from filters from leukapheresis. The study was approved by the ethics committee of the Charité—Universitätsmedizin Berlin (registration number EA1-157-13).

TABLE 2

Patient characteristics of CRC tumor tissue samples.

| | |
|---|---|
| Number of patients | 86 |
| Gender | 42 female/44 male |
| Age | Median 67 years (range: 22-85 years) |
| Tumor localization | Cecum (n = 8), colon (n = 56), rectum (n = 22) |
| Tumor grade* | G1 (n = 4), G2 (n = 47), G3 (n = 35) |

*Definition according to the WHO Classification of Tumours of the Digestive System[12]

Histopathology. Thin sections of archived patient samples (1-2 μm) were either stained with H&E or subjected to heat-induced epitope retrieval prior to incubation with antibodies specific for CES-1 (clone EP1376Y; Biozol Diagnostica, Eching, Germany) or CES-2 (#ab64867, polyclonal rabbit; Abcam; Cambridge, United Kingdom). These were visualized using the EnVision+HRP System (#K4011; Dako, Glostrup, Denmark), with diaminobenzidine (DAB; Dako) as chromogen. The nuclei were counterstained with hematoxylin and slides cover-slipped with glycerol gelatin (both Merck, Darmstadt, Germany). The AxioImager Z1 microscope (Carl Zeiss MicroImaging, Jena, Germany) was used for image acquisition. All evaluations were performed in a blinded manner.

Figure 3:
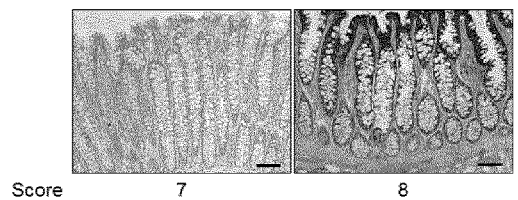
Figure 3:
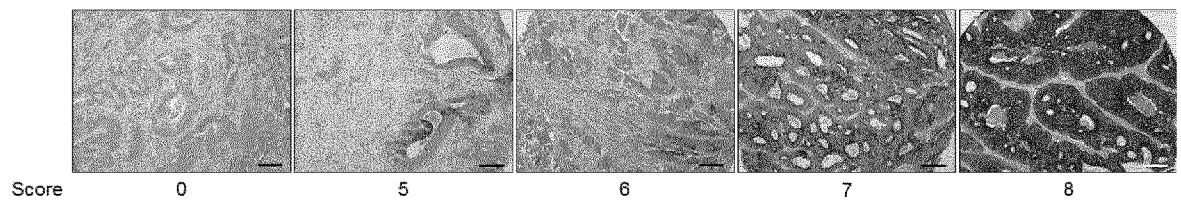

To evaluate CES expression in tissue samples, the expression levels and the percentages of CES-expressing tumor cells were added to create an overall score from 2 to 8 as follows: Expression level—1, low expression; 2, medium expression; 3, strong expression. Percentage—1, <10%; 2, 10 30%; 3, 31 60%; 4, 61 90%; 5, >90% (FIG. 3).

For detection of CES-2+ leukocytes, sections were subjected to a heat-induced epitope retrieval step prior to blocking of endogenous alkaline phosphatase (AP), using the Dual Endogenous Enzyme-Blocking Reagent (Dako). After rinsing, sections were incubated with anti-CES-2 antibodies, followed by biotinylated goat anti-rabbit antibodies (Dianova, Hamburg, Germany) and AP-labelled streptavidin (Dako). AP was visualized with the VECTOR Blue substrate kit (#SK-5300; Vector Laboratories, Burlingame, USA). Proteins were then inactivated by pressure cooking and the sections were incubated with antibodies specific for CD3 (clone M-20; Santa Cruz, San Diego, USA), CD11b (clone EP1345Y; Abcam), CD20 (clone L26; Dako), CD68 (clone PG M1; Dako), CD138 (clone MI15; Dako), CD163 (clone 10D6; Leica Biosystems, Nussloch, Germany) or MPO (#A0389, polyclonal rabbit; Dako) followed by biotinylated secondary antibodies (anti-goat, anti-mouse or anti-rabbit; Life Technologies, Carlsbad, USA) and AP-labelled streptavidin (Dako). AP was visualized with the chromogen FastRed (Dako). The nuclei were counterstained, the slides cover-slipped as described above, and the images acquired using the AxioImager Z1 microscope. As FastRed and Vector Blue are both fluorescent, coexpression was also detected using fluorescence microscopy (emission peaks: Red/560 nm, Vector Blue/680 nm). For immunohistochemical detection of CES-2 expressing plasma cells, sections were subjected to heat-induced epitope retrieval step prior to blocking of endogenous AP employing Dual Endogenous Enzyme-Blocking Reagent (Dako). This was followed by incubation with anti-MUM1 (clone MUM1p, Dako) followed by the LSAB™+, Dako REAL™ Detection System (#K5005, Dako). After color development, the proteins were inactivated by pressure cooking and endogenous peroxidase was blocked by Peroxidase-blocking solution (Dako). Sections were incubated with anti-CES-2 followed by the EnVision+ HRP System and DAB. Nuclei were counterstained with hematoxylin and slides cover-slipped with glycerol gelatin. Additionally, immunohistochemistry and—fluorescence were combined for costaining of CES-2 and CD138. Sections were subjected to a heat-induced epitope retrieval step prior to blocking of endogenous AP employing Dual Endogenous Enzyme-Blocking Reagent (Dako). After rinsing, sections were incubated with anti-CES-2 followed by biotinylated goat anti-rabbit antibodies (Dianova) and AP-labelled streptavidin (Dako). AP was visualized with LSAB™+, Dako REAL™ Detection System. Proteins were then inactivated by pressure cooking and the sections were incubated with anti-CD138 (clone MI15; Dako) followed by biotinylated anti-mouse secondary antibody and Alexa488-labelled streptavidin (Invitrogen). Nuclei were counterstained with DAPI (Sigma-Aldrich, St. Louis, USA) and sections cover-slipped with Fluoromount G (BIOZOL, Eching, Germany). Negative controls were carried out as above, omitting the primary antibodies.

Human cell lines. Human cell lines were from the American Type Culture Collection (ATCC; Bethesda, USA) or the German Collection of Microorganisms and Cell Cultures (DSMZ; Braunschweig, Germany). Burkitt's lymphoma-derived Raji cells (ATCC CCL86) and T cell leukemia-derived Jurkat cells (DSMZ ACC282) were used as models for lymphoblastoid; diffuse histiocytic lymphoma-derived U937 cells (ATCC CRL1593) and chronic myelogenous leukemia-derived K562 cells (ATCC CCL243) for myeloid; colorectal adenocarcinoma-derived HT-29 cells (ATCC HTB38) and embryonic kidney-derived HEK293 cells (ATCC CRL1573) for epithelial cells. All cell lines were maintained in standard culture medium consisting of RPMI1640 (Gibco; Life Technologies, Darmstadt, Germany) supplemented with 10% fetal bovine serum (Linaris, Bettingen, Germany), 2 mmol/L L-glutamine and 1 mmol/L sodium pyruvate (both from Biochrom, Berlin, Germany). For passaging twice weekly, cells were detached with trypsin (0.25%)/ethylenediaminetetraacetic acid (1 mmol/L; Life Technologies). Cells were routinely tested using a Mycoplasma-specific polymerase chain reaction (Venor-GEM; Biochrom) and positive cells were discarded. Detached cells from standard culture ($2 \times 10^8$) were fixed with formaldehyde and collected in paraffin blocks as described earlier [14].

Peripheral blood mononuclear cells (PBMC). PBMC were prepared using Ficoll density gradient centrifugation (p=1.078 g/mL; GE Healthcare, Frankfurt, Germany) according to the manufacturer's instructions. For immunocytochemistry, $2 \times 10^5$ freshly prepared PBMC were spun to slides using a Shandon cytospin centrifuge (Thermo Fisher Scientific, Waltham, USA).

Quantitative real-time polymerase chain reaction (PCR). If not noted otherwise, reagents were purchased from Life Technologies. Total RNA (1 µg) from PBMC and cell lines (5 $10 \times 10^6$) prepared by RNApure (Peqlab, Erlangen, Germany) was subjected to reverse transcription using the High Capacity cDNA Reverse Transcription Kit. The mRNA expression was assessed by TaqMan° PCR using the following Gene Expression Assays: CES1 (#Hs00275607_m1), CES2 (#Hs01077945_m1) and glyceraldehyde 3-phosphate dehydro-genase (GAPDH; #Hs99999905_m1) and the TaqMan® Universal PCR Master Mix in a StepOne Plus® device (all from Applied Biosystems, Foster City, USA). For quantification, reference sequences for each of the transcripts were cloned into pCR2.1 TOPO (Invitrogen, Groningen, The Netherlands) and used in standard titration curves from 102 to 109 copies. Expression of CES-1 and CES-2 was quantified in relation to GAPDH.

Statistics. The software GraphPad Prism 6 (Prism Software, San Diego, USA) was used for statistics tests. P values≤0.05 were considered significant.

REFERENCES

[1] T. Satoh, M. Hosokawa, Structure, function and regulation of carboxylesterases, Chemico-biological interactions, 162 (2006) 195-211.

[2] S.C. Laizure, V. Herring, Z. Hu, K. Witbrodt, R. B. Parker, The role of human carboxylesterases in drug metabolism: have we overlooked their importance?, Pharmacotherapy, 33 (2013) 210-222.

[3] T. Imai, M. Taketani, M. Shii, M. Hosokawa, K. Chiba, Substrate specificity of carboxylesterase isozymes and their contribution to hydrolase activity in human liver and small intestine, Drug metabolism and disposition: the biological fate of chemicals, 34 (2006) 1734-1741.

[4] T. Tsuji, N. Kaneda, K. Kado, T. Yokokura, T. Yoshimoto, D. Tsuru, CPT-11 converting enzyme from rat serum: purification and some properties, Journal of pharmacobio-dynamics, 14 (1991) 341-349.

[5] G. Xu, W. Zhang, M. K. Ma, H. L. McLeod, Human carboxylesterase 2 is commonly expressed in tumor tissue and is correlated with activation of irinotecan, Clinical cancer research: an official journal of the American Association for Cancer Research, 8 (2002) 2605-2611.

[6] C. Zhang, Y. Xu, Q. Zhong, X. Li, P. Gao, C. Feng, Q. Chu, Y. Chen, D. Liu, In vitro evaluation of the inhibitory potential of pharmaceutical excipients on human carboxylesterase 1A and 2, PloS one, 9 (2014) e93819.

[7] X. Tang, H. Wu, Z. Wu, G. Wang, Z. Wang, D. Zhu, Carboxylesterase 2 is downregulated in colorectal cancer following progression of the disease, Cancer investigation, 26 (2008) 178-181.

[8] M. A. Schiel, S. L. Green, W. I. Davis, P. C. Sanghani, W. F. Bosron, S. P. Sanghani, Expression and characterization of a human carboxylesterase 2 splice variant, The Journal of pharmacology and experimental therapeutics, 323 (2007) 94-101.

[9] H. Nishimuta, J. B. Houston, A. Galetin, Hepatic, intestinal, renal, and plasma hydrolysis of prodrugs in human, cynomolgus monkey, dog, and rat: implications for in vitro-in vivo extrapolation of clearance of prodrugs, Drug metabolism and disposition: the biological fate of chemicals, 42 (2014) 1522-1531.

[10] N. Silvestris, G. Simone, G. Partipilo, E. Scarpi, V. Lorusso, A. E. Brunetti, E. Maiello, A. Paradiso, A. Mangia, CES2, ABCG2, TS and Topo-I primary and synchronous metastasis expression and clinical outcome in metastatic colorectal cancer patients treated with first-line FOLFIRI regimen, International journal of molecular sciences, 15 (2014) 15767-15777.
[11] M. Taketani, M. Shii, K. Ohura, S. Ninomiya, T. Imai, Carboxylesterase in the liver and small intestine of experimental animals and human, Life sciences, 81 (2007) 924-932.
[12] F. T. C. Bosman, F.; Hruban, R. H.; Theise, N. D., WHO classification of tumours of the digestive system., in: F. T. C. Bosman, F.; Hruban, R. H.; Theise, N. D. (Ed.) WHO classification of tumours of the digestive system, World health Organisation, Geneva, Switzerland, 2010.
[13] L. H. Sobin, Gospodarowicz, M. K., Wittekind, C., TNM Classification of Malignant Tumours, Wiley-Blackwell, 2009, pp. 336.
[14] C. Zanini, M. Forni, The cell block technique revisited for cells cultured in adherence and as "spheres", Histochemistry and cell biology, 140 (2013) 685-690.
[15] F. P. O'Connell, J. L. Pinkus, G. S. Pinkus, CD138 (syndecan-1), a plasma cell marker immunohistochemical profile in hematopoietic and nonhematopoietic neoplasms, American journal of clinical pathology, 121 (2004) 254-263.
[16] B. Falini, M. Fizzotti, A. Pucciarini, B. Bigerna, T. Marafioti, M. Gambacorta, R. Pacini, C. Alunni, L. Natali-Tanci, B. Ugolini, C. Sebastiani, G. Cattoretti, S. Pileri, R. Dalla-Favera, H. Stein, A monoclonal antibody (MUM1p) detects expression of the MUM1/IRF4 protein in a subset of germinal center B cells, plasma cells, and activated T cells, Blood, 95 (2000) 2084-2092.
[17] S. Guichard, C. Terret, I. Hennebelle, I. Lochon, P. Chevreau, E. Fretigny, J. Selves, E. Chatelut, R. Bugat, P. Canal, CPT-11 converting carboxylesterase and topoisomerase activities in tumour and normal colon and liver tissues, British journal of cancer, 80 (1999) 364-370.
[18] F. A. Farraye, R. D. Odze, J. Eaden, S. H. Itzkowitz, AGA technical review on the diagnosis and management of colorectal neoplasia in inflammatory bowel disease, Gastroenterology, 138 (2010) 746-774, 774 e741-744; quiz e712-743.
[19] S. Chakrabarty, Regulation of human colon-carcinoma cell adhesion to extracellular matrix by transforming growth factor beta 1, International journal of cancer. Journal international du cancer, 50 (1992) 968-973.
[20] S. R. Lepri, L. C. Zanelatto, P. B. da Silva, D. Sartori, L. R. Ribeiro, M. S. Mantovani, Effects of genistein and daidzein on cell proliferation kinetics in HT29 colon cancer cells: the expression of CTNNBIP1 (beta-catenin), APC (adenomatous polyposis coli) and BIRCS (survivin), Human cell, 27 (2014) 78-84.
[21] E. Cecchin, G. Corona, S. Masier, P. Biason, G. Cattarossi, S. Frustaci, A. Buonadonna, A. Colussi, G. Toffoli, Carboxylesterase isoform 2 mRNA expression in peripheral blood mononuclear cells is a predictive marker of the irinotecan to SN38 activation step in colorectal cancer patients, Clinical cancer research : an official journal of the American Association for Cancer Research, 11 (2005) 6901-6907.
[22] W. Choi, D. Cogdell, Y. Feng, S. R. Hamilton, W. Zhang, Transcriptional activation of the carboxylesterase 2 gene by the p53 pathway, Cancer biology & therapy, 5 (2006) 1450-1456.
[23] S. Braggio, A. Ferrara, M. Sartori, M. Bottacini, U. Zanelli, L. Zonzini, M. Petrone, Evaluation of the role of intestinal and liver metabolism in the conversion of two different ester prodrugs of sanfetrinem to the parent drug in vitro and in vivo using different rat tissues and a surgically prepared rat model, European journal of pharmaceutical sciences : official journal of the European Federation for Pharmaceutical Sciences, 16 (2002) 45-51.
[24] W. Zhang, G. Xu, H.L. McLeod, Comprehensive evaluation of carboxylesterase-2 expression in normal human tissues using tissue array analysis, Applied immunohistochemistry & molecular morphology: AIMM/official publication of the Society for Applied Immunohistochemistry, 10 (2002) 374-380.
[25] J. S. Munger, G. P. Shi, E. A. Mark, D. T. Chin, C. Gerard, H. A. Chapman, A serine esterase released by human alveolar macrophages is closely related to liver microsomal carboxylesterases, The Journal of biological chemistry, 266 (1991) 18832-18838.
[26] V. Costes, V. Magen, E. Legouffe, L. Durand, P. Baldet, J. F. Rossi, B. Klein, J. Brochier, The Mil5 monoclonal antibody (anti-syndecan-1) is a reliable marker for quantifying plasma cells in paraffin-embedded bone marrow biopsy specimens, Human pathology, 30 (1999) 1405-1411.
[27] M. Bernfield, R. Kokenyesi, M. Kato, M. T. Hinkes, J. Spring, R. L. Gallo, E. J. Lose, Biology of the syndecans: a family of transmembrane heparan sulfate proteoglycans, Annual review of cell biology, 8 (1992) 365-393.
[28] A. Shimabukuro-Vornhagen, H. A. Schlosser, L. Gryschok, J. Malcher, K. Wennhold, M. Garcia-Marquez, T. Herbold, L. S. Neuhaus, H. J. Becker, A. Fiedler, P. Scherwitz, T. Koslowsky, R. Hake, D. L. Stippel, A. H. Holscher, S. Eidt, M. Hallek, S. Theurich, M. S. von Bergwelt-Baildon, Characterization of tumor-associated B-cell subsets in patients with colorectal cancer, Oncotarget, 5 (2014) 4651-4664.
[29] R. Khanna, C. L. Morton, M. K. Danks, P. M. Potter, Proficient metabolism of irinotecan by a human intestinal carboxylesterase, Cancer research, 60 (2000) 4725-4728.
[30] Y. T. Chen, L. Trzoss, D. Yang, B. Yan, Ontogenic expression of human carboxylesterase-2 and cytochrome P450 3A4 in liver and duodenum: postnatal surge and organ-dependent regulation, Toxicology, 330 (2015) 55-61.
[31] M. L. Cupi, M. Sarra, I. Marafini, I. Monteleone, E. Franze, A. Ortenzi, A. Colantoni, G. Sica, P. Sileri, M. M. Rosado, R. Carsetti, T. T. MacDonald, F. Pallone, G. Monteleone, Plasma cells in the mucosa of patients with inflammatory bowel disease produce granzyme B and possess cytotoxic activities, Journal of immunology, 192 (2014) 6083-6091.
[32] C. B. Westphalen, S. Asfaha, Y. Hayakawa, Y. Takemoto, D. J. Lukin, A. H. Nuber, A. Brandtner, W. Setlik, H. Remotti, A. Muley, X. Chen, R. May, C. W. Houchen, J. G. Fox, M. D. Gershon, M. Quante, T. C. Wang, Long-lived intestinal tuft cells serve as colon cancer-initiating cells, The Journal of clinical investigation, 124 (2014) 1283-1295.

The invention claimed is:

1. A method of stratifying and treating a patient suffering from biliary tract cancer (BTC), the method comprising the steps of
a) providing a BTC tumor sample of the patient,
b) determining the expression of carboxylesterase 2 (CES2) in the BTC tumor sample, wherein a lack of expression of CES2 in the BTC tumor sample indicates the risk of a patient that a treatment with an ester prodrug of a chemotherapeutic agent will not lead to a treatment success, and wherein the expression of CES2 in the BTC tumor sample indicates that a treatment with an ester prodrug of a chemotherapeutic agent will lead to a treatment success, and c) (i) treating the patient whose BTC tumor sample is determined to express CES2 with the ester prodrug of a chemotherapeutic, or (ii) treating the patient whose BTC tumor sample lacks CES2 expression with a treatment regimen that comprises a treatment that is different from the ester prodrug of a chemotherapeutic agent.

2. A method of assessing if a patient suffering from biliary tract cancer (BTC) is a responder to treatment with an ester prodrug of a chemotherapeutic agent and treating the patient if the patient is a responder, the method comprising the steps of a) providing a BTC tumor sample of the patient, b) determining the level of CES2 expression in the BTC tumor sample, wherein the expression of CES2 in the BTC tumor sample indicates that the patient is a responder to treatment with the ester prodrug of a chemotherapeutic agent, and wherein the lack of expression of CES2 in the BTC tumor sample indicates that the patient is a non-responder to treatment with the ester prodrug of a chemotherapeutic agent, and c) (i) treating the patient with the ester prodrug of a chemotherapeutic agent if the patient is a responder, or (ii) treating the patient with a treatment regimen that comprises a treatment that is different from the ester prodrug if the patient is a non-responder.

3. The method according to claim 2, wherein the ester prodrug is an ester prodrug of etoposide.

4. The method according to claim 3, wherein the ester-prodrug of etoposide is CAP7.1.

5. The method according to claim 1, the method consisting of:

a) providing a BTC tumor sample of the patient, b) determining the expression of carboxylesterase 2 (CES2) in the BTC tumor sample, wherein a lack of expression of CES2 in the BTC tumor sample indicates the risk of a patient that a treatment with an ester prodrug of a chemotherapeutic agent will not lead to a treatment success, and wherein the expression of CES2 in the BTC tumor sample indicates that a treatment with an ester prodrug of a chemotherapeutic agent will lead to a treatment success, and c) (i) treating the patient whose BTC tumor sample is determined to express CES2 with the ester prodrug of a chemotherapeutic, or (ii) treating the patient whose BTC tumor sample lacks CES2 expression with a treatment regimen that comprises a treatment that is different from the ester prodrug of a chemotherapeutic agent.

* * * * *